United States Patent [19]
Ramin

[11] Patent Number: 5,833,967
[45] Date of Patent: Nov. 10, 1998

[54] COLLOIDAL SILICA AS A REINFORCING AGENT OF KERATIN SUBSTANCES

[75] Inventor: Roland Ramin, Itteville, France

[73] Assignee: L'Oreal, Paris, France

[21] Appl. No.: 654,616

[22] Filed: May 29, 1996

[30] Foreign Application Priority Data

May 30, 1995 [FR] France .................................. 95 06386
May 30, 1995 [FR] France .................................. 95 06388
May 30, 1995 [FR] France .................................. 95 06389

[51] Int. Cl.⁶ ..................................... A61K 7/06
[52] U.S. Cl. .................. 424/70.4; 424/70.5; 424/70.51; 424/70.11; 424/70.16
[58] Field of Search ................. 424/70.4, 70.5, 424/70.51, 70.11, 70.16

[56] References Cited

U.S. PATENT DOCUMENTS

| | | | |
|---|---|---|---|
| 3,639,572 | 2/1972 | Heinrich | 424/61 |
| 3,654,936 | 4/1972 | Wajaroff | 424/70.4 |
| 3,975,515 | 8/1976 | Wajaroff | 424/70.5 |
| 4,177,260 | 12/1979 | Wajaroff | 424/70.5 |
| 4,859,459 | 8/1989 | Greiche | 424/70.51 |
| 4,983,418 | 1/1991 | Murphy et al. | 424/47 |
| 5,071,639 | 12/1991 | Soyama et al. | 424/61 |
| 5,352,783 | 10/1994 | Shafiee | 435/161 |

FOREIGN PATENT DOCUMENTS

| | | |
|---|---|---|
| 0453628 | 10/1990 | European Pat. Off. . |
| 0504754 | 3/1992 | European Pat. Off. . |
| 0529396 | 8/1992 | European Pat. Off. . |
| 0635260 | 7/1994 | European Pat. Off. . |
| 2578741 | 9/1985 | France . |
| 2053505 | 10/1970 | Germany . |
| 2205461 | 2/1972 | Germany . |
| 3206448 | 2/1982 | Germany . |
| WO 94/28877 | 6/1994 | WIPO . |

OTHER PUBLICATIONS

Chemical Abastract Vol. 89, 1978, p. 358.
Wenninger J.A., McEwan G.N., Int'l Cosmetic Ingredient Dictionary, Vol. 2, 1993, p. 801.

*Primary Examiner*—Paul R. Michl
*Attorney, Agent, or Firm*—Finnegan, Henderson, Farabow, Garrett & Dunner, L.L.P.

[57] ABSTRACT

A method of reinforcing keratin substances using colloidal silicic acid. The colloidal silicic acid may be present as a reinforcing agent in a composition to be applied to the keratin substances. This composition may be in the form of a nail varnish or base, a hair product, a mascara, or a base in an oily medium.

22 Claims, No Drawings

COLLOIDAL SILICA AS A REINFORCING AGENT OF KERATIN SUBSTANCES

The present invention relates to a method of reinforcing keratin substances using colloidal silicic acid, e.g. by applying the colloidal silicic acid to the keratin substances. More particularly, the present invention relates to such a method wherein the colloidal silicic acid is present as a reinforcing agent in a cosmetic composition in a solvent medium to be applied to the keratin substances. This cosmetic composition may be in the form of a nail varnish or base, a hair product or a mascara, or a base in an oily medium.

Colloidal silicic acid has frequently been used in cosmetic compositions. For example, WO 94/28877 (the disclosure of which is incorporated specifically by reference herein) shows that small quantities (1–500ppm) of colloidal silicic acid enhances the penetration of water, oils and collagen into the epidermis and the penetration of coloring material into hair shafts.

Compositions to be applied, for example to the nails, of the nail varnish type or care base type for the nails in a solvent medium are known, these compositions usually comprising at least one film-forming polymer, optionally a plasticizer, pigments, Theological agents and solvents.

Such a composition may make it possible to paint the nail without, however, treating it. It would thus be advantageous to have available a cosmetic composition which, on the one hand, could paint the nail by depositing a cosmetically acceptable film thereon, and which, on the other hand, would be capable of reinforcing the keratin substances of the nail, by virtue of the presence of a suitable active agent, referred to hereinafter in the present specification as a "reinforcing agent".

Aqueous nail varnishes generally comprise an aqueous dispersion of particles of film-forming polymer, to which may be added co-solvents, pigments and/or dyes, as well as rheological agents. Varnishes of adequate viscosity are thus obtained, which can be applied easily to the nails, in a sufficient amount, and which are of good thixotropy. It may, however, be necessary to have available a composition capable of reinforcing keratin substances, for example nails, eyelashes or hair, and which would thus contain a suitable active agent or "reinforcing agent".

Treatment bases to be applied especially to the nail are known which are provided in the form of an oil or a mixture of oils, capable of containing customary additives such as colorants and/or active agents, for treating, nourishing, caring for and/or beautifying the nail.

There is still, however, the need for a base in an oily medium, comprising an active agent or reinforcing agent capable of strengthening keratinous materials, especially nails.

The function of such a reinforcing agent is to make it possible, for example in the case of a composition to be applied to the nails, to reduce the fragility of weakened nails and, in particular, striated, cracked, soft or flexible nails and nails having a tendency to split.

Applicant has observed, surprisingly, that colloidal silicic acid could be used satisfactorily as an agent for reinforcing keratin substances, in particular of the nails, but also of the hair and eyelashes.

The present invention relates to the use of colloidal silicic acid as an agent for reinforcing keratin substances, e.g. in a method which comprises applying to the keratin substances an effective amount of colloidal silicic acid.

The present invention also relates to the use of colloidal silicic acid as an agent for reinforcing keratin substances, in a composition comprising at least one film-forming material and at least one solvent.

The solvent can be an organic solvent and/or water. When the solvent is water the film forming material preferentially comprises particles of film-forming polymer dispersed in an aqueous medium.

Another subject of the invention is the use of colloidal silicic acid as agent for strengthening keratinous materials, in a composition comprising an oily medium.

The use of a composition according to the invention, for example on the nails, makes it possible to obtain harder and stronger nails, which are thus less brittle. This reinforcement of nail keratin also makes it possible to obtain nails which no longer split and/or which no longer crack.

When the composition according to the invention is a composition in an organic solvent, it thus comprises at least one film-forming material which may be chosen, in particular, from alkyd, acrylic and/or vinyl resins, polyurethanes and polyesters, celluloses and cellulose derivatives such as nitrocellulose, and resins resulting from the condensation of formaldehyde with an arylsulphonamide, and mixtures thereof.

The film-forming material is generally in solution, for example at a concentration ranging from 5 to 25% by weight, in an organic solvent such as toluene, xylene, ethyl acetate and/or butyl acetate, ketones, glycol ethers, esters or alcohols such as ethanol, isopropanol or butanol, and mixtures thereof.

The composition may also comprise a plasticizer and optionally rheological agents.

Among the plasticizers which may be mentioned are citrates, phthalates, esters and/or camphor, generally used in an amount ranging from 5 to 30% by weight relative to the weight of the composition.

Among the rheological agents which may be mentioned are organophilic bentonites, cellulose derivatives, crosslinked polyacrylic acid derivatives, guar gums and carob gums, as well as xanthan gums.

The composition according to the invention can also comprise particles of film-forming polymer dispersed in an aqueous medium.

Among the film-forming polymers which may be used, mention may be made of polyurethanes, for example anionic polyurethanes, polyester-polyurethanes, polyether-polyurethanes, radical polymers in particular of acrylic, acrylic styrene and/or vinylic type, polyesters and alkyd resins, alone or as a mixture.

The dispersion may also comprise an associative polymer of polyurethane type or a natural gum such as xanthan gum.

The dispersion preferably has a solids content ranging from 30 to 45% by weight relative to the weight of the composition.

The composition according to the invention can also comprise an oily medium. Preferably, it is provided in the form of a base in an oily medium. The oily medium may comprise one or more oils, which are volatile and/or nonvolatile, for example of plant, mineral, animal and/or synthetic origin, among which there may be mentioned:

animal or vegetable oils formed by esters of fatty acids and polyols, in particular liquid triglycerides, for example sunflower, maize, soya bean, gourd, grapeseed, sesame, hazelnut, apricot, sweet-almond or avocado oils, fish oils, glycerol tricaprocaprylate, or vegetable or animal oils of formula $R_9COOR_{10}$ in which $R_9$ represents the residue of a higher fatty acid comprising from 7 to 19 carbon atoms and $R_{10}$ represents a branched hydrocarbon chain containing from 3 to 20 carbon atoms, for example Purcellin oil;

natural or synthetic essential oils such as, for example, eucalyptus, lavandin, lavender, vetiver, lemon, sandalwood, rosemary, camomile, savory, nutmeg, cinnamon, hyssop, caraway, orange, geraniol, cade and bergamot oil;

hydrocarbons such as hexadecane and paraffin oil;

esters of an inorganic acid and an alcohol;

ethers and polyethers; and silicone oils and gums.

In a specific embodiment, the oily medium may also comprise an aqueous phase, with which it can form a solution, or an oil-in-water or a water-in-oil emulsion, or even a multiple emulsion.

According to the invention, the colloidal silicic acid in the composition is a pyrogenic or surface-treated silica, which may be in the form of hydrophilic pyrogenic silica, hydrophobic pyrogenic silica or silica surface-treated by an organic treatment.

Pyrogenic silicas may be obtained by high-temperature hydrolysis of a volatile silicon compound in an oxyhydrogen flame. This results in the production of a finely divided silica. The surface of the said silica may be chemically modified by reaction, by reduction of the number of silanol groups, in order to obtain a hydrophobic silica.

The colloidal silicic acid preferably has a particle size which may be nanometric to micrometric, for example of about 10–200 nm.

The colloidal silicic acid according to the invention may be chosen, inter alia, from the compounds sold by Degussa under the brand names Aerosil 200, Aerosil 300 or Aerosil 380, which are hydrophilic silicas, Aerosil MOX80 or Aerosil COK84, which are special silicas, Aerosil R972, which is a hydrophobic silica, or alternatively Aerosil OK412, which is a surface-treated silica.

In the embodiment when the composition according to the invention comprises at least one film-forming material and at least one solvent, the composition may comprise the colloidal silicic acid in an amount ranging from 0.1% to 5% by weight, preferably in an amount ranging from 1 to 2% by weight, relative to the total weight of the composition.

In the embodiment when the composition comprises an oily medium, the composition may comprise the colloidal silicic acid in a quantity ranging from 0.1 to 10% by weight, preferably in a quantity ranging from 0.3 to 3% by weight, relative to the total weight of the composition.

The composition according to the invention may also comprise any additive known to those skilled in the art as being capable of being incorporated into such a composition, such as spreading agents, wetting agents, dispersing agents, antifoaming agents, preserving agents, UV screening agents, dyes, pigments, pearlescent agents, active agents such as N-butylformal, D-panthenol, phytanetriol, vitamins and derivatives thereof, keratin and derivatives thereof, melanin, collagen, cystine, chitosan and derivatives thereof, ceramides, biotin, trace elements, glycerol, protein hydrolysates, phospholipids and moisturizing agents. It is apparent that a person skilled in the art will take care to select this or these optional additional compounds, and/or the amount thereof, such that the advantageous properties of the composition according to the invention are not, or are substantially not damaged by the addition envisaged.

The composition according to the invention may be prepared by a person skilled in the art based on his or her general knowledge and according to the state of the art.

The composition according to the invention may be in the form of a product to be applied to the nails, such as a varnish, a base or a care base; in the form of a product to be applied to the eyelashes, such as a mascara; or in the form of a hair product, such as a styling mousse, lotion or lacquer.

The examples which follow serve to illustrate the invention without, however, being limiting in nature.

EXAMPLE 1

A nail varnish having the following composition (% by weight) was prepared:

| | |
|---|---|
| nitrocellulose | 15% |
| plasticizer and resin | 15% |
| colloidal silicic acid (Aerosil 200 from Degussa) | 1% |

A varnish of adequate texture was obtained, which was easily applied to the nail. After drying, it allowed a smooth and uniform film to be obtained.

EXAMPLE 2

The varnish of Example 1 was compared with a control varnish of the composition:

| | |
|---|---|
| nitrocellulose | 15% |
| plasticizer and resin | 15% |
| solvent (ethyl acetate and butyl acetate) qs | 100% |

This composition was applied for 8 weeks to embrittled nails (striated, cracked, soft or flexible nails and nails having a tendency to split).

The varnish of Example 1 was applied to all the nails on one hand only, the control varnish being applied to the other hand.

The following results were observed, obtained by comparative self-evaluation: an improvement in the state of the nails which received the composition according to the invention (varnish of Example 1) was found. The nails are more solid and stronger, they are less brittle and they split less.

EXAMPLE 3

A nail varnish having the following composition (% by weight) is prepared:

| | |
|---|---|
| nitrocellulose | 10% |
| plasticizer and resin | 15% |
| colloidal silicic acid (Aerosil 200 from Degussa) | 1.5% |
| particles of mother-of-pearl | 0.2% |
| pigment | 0.5% |
| active agents, dyes and additives | 1% |
| solvent (ethyl acetate and butyl acetate) qs | 100% |

A varnish which can be applied easily to the nail was obtained. After drying, it allowed a smooth and uniform film to be obtained.

Evaluation Test

The varnish of Example 1 underwent an evaluation test on a panel of women, who were divided into two categories: those having soft nails (first category) and those having hard nails (second category). These women applied the varnish of Example 1 for 8 weeks and evaluated (rating from 1 to 5)

after 4 weeks ($N_1$) and after 8 weeks of treatment ($N_2$): the hardness, the sheen, the smooth appearance, the brittle nature, the splitting and the general state of their nails. The same evaluation ($N_0$) was made before the start of the treatment. An average of these evaluations was determined, which was then converted into a percentage improvement in the average rating after four ($M_1$) and after eight weeks ($M_2$) relative to the average rating after treatment:

$$M_i = (N_i - N_0)/N_0$$

i=1, 2

Results

For the women who, at the start of the study, had soft nails (17 cases):

|  | $M_1$ | $M_2$ |
| --- | --- | --- |
| Hardness Improvement of hardness | 55% | 50% |
| Brittle nails Reduction of brittle nature | 28% | 38% |
| Splitting Reduction of splitting | 31% | 31% |
| General state Improvement | 41% | 36% |

For the women who, at the start of the study, had hard nails (13 cases):

|  | $M_1$ | $M_2$ |
| --- | --- | --- |
| Sheen Improvement of sheen | 20% | 28% |
| Smooth appearance Improvement | 45% | 60% |
| Brittle nails Reduction of brittle nature | 40% | 54% |
| Splitting Reduction of splitting | 37% | 50% |
| General state Improvement | 52% | 52% |

It is seen that these improvements as a whole were significant from 1 month and then stabilized.

EXAMPLE 4

A nail varnish having the following composition (% by weight) was prepared:

| dispersion of acrylic polymer (40% solids content) | 38% |
| --- | --- |
| dispersion of polyurethane (30% solids content) | 50% |
| colloidal silicic acid (Aerosil MOX80) | 0.7% |
| additives (dyes, active agents) | 1.3% |
| water | qs 100% |

A varnish was obtained, which could be applied easily to the nail, and which, after drying, allowed a cosmetically acceptable film to be obtained.

EXAMPLE 5

The varnish of Example 4 was compared with a control varnish of composition:

| dispersion of acrylic polymer (40% SC) | 38% |
| --- | --- |
| dispersion of polyurethane (30% SC) | 50% |

-continued

| additives (dyes, active agents) | 1.3% |
| --- | --- |
| water | qs 100% |

These two compositions were applied for 8 weeks to embrittled nails (striated, cracked, soft or flexible nails and nails having a tendency to split). The varnish according to Example 4 was applied to all the nails on one hand only, the control varnish being applied to the other hand. The following results were observed, obtained by comparative self-evaluation: an improvement in the state of the nails which received the varnish according to the invention was found. The nails were more solid and stronger, they were less brittle and they split less.

EXAMPLE 6

A nail treatment base having the following composition was prepared:

| vegetable oil | 5% |
| --- | --- |
| colloidal silicic acid | 1% |
| volatile silicone oil | 94% |

A nail treatment oil was obtained which deposited a film protecting the nail, which penetrated by massage at the level of the ungual matrix and bed.

EXAMPLE 7

The treatment base according to Example 6 was compared with a control base having the following composition:

| vegetable oil | 5% |
| --- | --- |
| volatile silicone oil | 95% |

These compositions were applied for 8 weeks to embrittled nails (grooved, cracked, soft or supple, and tending to split).

The base of Example 6 was applied to all the nails of one hand, the control base being applied to the other hand.

The following results, obtained by comparative self-evaluation, were observed: an improvement was observed in the state of the nails which received the base according to the invention. The nails were stronger and more resistant; they were less brittle and split less.

EXAMPLE 8

A nail treatment base having the following composition was prepared:

| vegetable oil | 4% |
| --- | --- |
| mineral oil | 1% |
| colloidal silicic acid | 0.5% |
| additives (active agents and colorants) | 1.5% |
| solvent | 1% |
| volatile silicone oil | 92% |

A nail treatment oil was obtained which deposited a film protecting the nail, which penetrated by massage at the level of the ungual matrix and bed.

I claim:

1. A method of reinforcing keratin substances which comprises applying to the keratin substances an effective amount of colloidal silicic acid, wherein said colloidal silicic acid is present in a composition comprising at least one organic solvent and at least one film-forming material selected from alkyd resins, acrylic resins, vinyl resins, polyurethanes, polyesters, celluloses and cellulose derivatives, and resins resulting from the condensation of formaldehyde with an arylsulphonamide.

2. A method of reinforcing keratin substances according to claim 1, wherein said cellulose derivatives include nitrocellulose.

3. A method of reinforcing keratin substances which comprises applying to the keratin substances an effective amount of colloidal silicic acid, wherein said colloidal silicic acid is present in a composition comprising at least one film-forming material and at least one organic solvent, and further wherein said at least one organic solvent is selected from toluene, xylene, ethyl acetate, butyl acetate, ketones, glycol ethers, esters and alcohols.

4. A method of reinforcing keratin substances according to claim 3, wherein said alcohols include ethanol, isopropanol and butanol.

5. A method of reinforcing keratin substances according to claim 3, wherein said at least one film-forming material is present in concentrations ranging from 5 to 25% by weight, relative to the weight of the composition.

6. A method of reinforcing keratin substances which comprises applying to the keratin substances an effective amount of colloidal silicic acid, wherein said colloidal silicic acid is present in a composition comprising at least one film-forming material and at least one solvent, wherein said composition also comprises at least one plasticizer.

7. A method of reinforcing keratin substances which comprises applying to the keratin substances an effective amount of colloidal silicic acid, wherein said colloidal silicic acid is present in a composition comprising at least one film-forming material and at least one solvent, wherein said composition also comprises at least one rheological agent.

8. A method of reinforcing keratin substances according to claim 6, wherein said at least one plasticizer is selected from citrates, phthalates, esters, and camphor.

9. A method of reinforcing keratin substances according to claim 6, wherein said at least one plasticizer is present in an amount ranging from 5 to 30% by weight, relative to the weight of the composition.

10. A method of reinforcing keratin substances according to claim 7, wherein said at least one rheological agent is selected from organophilic bentonites, cellulose derivatives, crosslinked polyacrylic acid derivates, guar gums, carob gums, and xanthan gums.

11. A method of reinforcing keratin substances which comprises applying to the keratin substances an effective amount of colloidal silicic acid, wherein said colloidal silicic acid is present in a composition comprising at least one solvent and at least one film-forming material selected from polyurethanes, polyeste-polyurethanes, polyetherpolyurethanes, radical polymers, polyesters and alkyd resins, wherein said at least one solvent is water and the particles of said at least one film-forming material are dispersed in an aqueous medium.

12. A method of reinforcing keratin substances according to claim 11, wherein said radical polymers are selected from acrylic, acrylic styrene and vinylic type radical polymers.

13. A method of reinforcing keratin substances according to claim 11, wherein said composition also comprises an associative polymer of polyurethane type or a natural gum.

14. A method of reinforcing keratin substances according to claim 11, wherein said dispersed film-forming material has a solids content ranging from 30 to 45% by weight, relative to the weight of the composition.

15. A method of reinforcing keratin substances which comprises applying to the keratin substances an effective amount of colloidal silicic acid, wherein said colloidal silicic acid is present in a composition comprising at least one film-forming material, at least one solvent, and an oily medium.

16. A method of reinforcing keratin substances according to claim 15, wherein said colloidal silicic acid is present in a quantity ranging from 0.01 to 10% by weight, relative to the total weight of the composition.

17. A method of reinforcing keratin substances according to claim 15, wherein said oily medium comprises at least one oil selected from volatile and nonvolatile oils of plant, mineral, animal, and synthetic origin.

18. A method of reinforcing keratin substances according to claim 17, wherein said at least one oil of plant, mineral, animal and synthetic origin is selected from the esters of fatty acids and polyols; sunflower, maize, soya bean, gourd, grapeseed, sesame, hazelnut, apricot, sweet-almond, and avocado oils; fish oils; glycerol tricaprocaprylate; vegetable and animal oils of formula $R_9COOR_{10}$ in which $R_9$ represents the residue of a higher fatty acid comprising from 7 to 19 carbon atoms and $R_{10}$ represents a branched hydrocarbon chain containing from 3 to 20 carbon atoms; natural and synthetic essential oils; hydrocarbons; esters of an inorganic acid and an alcohol; ethers, polyethers; and silicone oils.

19. A method of reinforcing keratin substances according to claim 18, wherein said oils of formula $R_9COOR_{10}$ include Purcellin oil; said natural and synthetic essential oils are selected from eucalyptus, lavandin, lavender, vetiver, lemon, sandalwood, rosemary, camomile, savory, nutmeg, cinnamon, hyssop, caraway, orange, geraniol, cade and bergamot oil; and said hydrocarbons are selected from hexadecane and paraffin oil.

20. A method of reinforcing keratin substances according to claim 15, wherein said oily medium also comprises an aqueous phase with which it may form a solution, an oil-in-water emulsion, a water-in-oil emulsion, or a multiple emulsion.

21. A method of reinforcing keratin substances according to claim 15, wherein the composition is in the form of an oily base or an emulsion.

22. A method of reinforcing keratin substances according to claim 21, wherein said composition is a nail treatment base, a hair oil, gel or cream, or a treatment mascara.

* * * * *